(12) United States Patent
Jaffe et al.

(10) Patent No.: US 7,815,677 B2
(45) Date of Patent: Oct. 19, 2010

(54) REINFORCEMENT DEVICE FOR A BIOLOGICAL VALVE AND REINFORCED BIOLOGICAL VALVE

(75) Inventors: Norman Jaffe, Dana Point, CA (US); Afksendiyos Kalangos, Geneva (CH); Yuri Zhivilo, Moscow (RU)

(73) Assignee: Leman Cardiovascular SA, Morges (CH)

( * ) Notice: Subject to any disclaimer, the term of this patent is extended or adjusted under 35 U.S.C. 154(b) by 437 days.

(21) Appl. No.: 11/775,043

(22) Filed: Jul. 9, 2007

(65) Prior Publication Data

US 2009/0018649 A1 Jan. 15, 2009

(51) Int. Cl.
*A61F 2/24* (2006.01)

(52) U.S. Cl. .................................. 623/2.14

(58) Field of Classification Search ........ 623/2.12–2.19
See application file for complete search history.

(56) References Cited

U.S. PATENT DOCUMENTS

| | | | |
|---|---|---|---|
| 3,983,581 A | 10/1976 | Angell et al. | |
| 4,247,292 A | 1/1981 | Angell | |
| 4,345,340 A | 8/1982 | Rosen | |
| 4,364,126 A | 12/1982 | Rosen et al. | |
| 4,506,394 A | 3/1985 | Bedard | |
| 4,535,483 A | 8/1985 | Klawitter et al. | |
| 4,666,442 A | 5/1987 | Arru et al. | |
| 4,692,164 A | 9/1987 | Dzemeshkevich et al. | |
| 4,755,593 A | 7/1988 | Lauren | |
| 4,851,000 A | 7/1989 | Gupta | |
| 5,037,434 A | 8/1991 | Lane | |
| 5,178,633 A | 1/1993 | Peters | |
| 5,352,240 A | 10/1994 | Ross | |
| 5,549,665 A | 8/1996 | Vesely et al. | |
| 5,554,185 A | 9/1996 | Block et al. | |
| 5,595,571 A | 1/1997 | Jaffe et al. | |
| 5,713,953 A | 2/1998 | Vallana et al. | |
| 5,720,777 A | 2/1998 | Jaffe et al. | |
| 5,843,180 A | 12/1998 | Jaffe et al. | |
| 5,843,181 A | 12/1998 | Jaffe et al. | |
| 5,865,723 A | 2/1999 | Love | |
| 6,059,827 A | 5/2000 | Fenton, Jr. | |

(Continued)

FOREIGN PATENT DOCUMENTS

EP 0850607 A 7/1998

(Continued)

OTHER PUBLICATIONS

International Search Report for International Application No. PCT/IB2004/000707, dated Jun. 30, 2004.

(Continued)

*Primary Examiner*—Suzette J Gherbi
(74) *Attorney, Agent, or Firm*—Knobbe, Martens, Olson & Bear, LLP

(57) ABSTRACT

A reinforcement device for a biological valve includes an arrangement of supports configured to establish a double-trigone geometry in the valve and coupled to a base upon which the valve may be mounted. A plurality of commissural supports establish the geometry of a commissural trigone, and a plurality of intercommissural supports establish the geometry of an intercommissural trigone. A method for reinforcing a biological valve includes using commissural supports in conjunction with intercommissural supports, both sets of supports coupled to a base upon which the valve is mounted.

36 Claims, 5 Drawing Sheets

U.S. PATENT DOCUMENTS

| | | | |
|---|---|---|---|
| 6,168,614 | B1 | 1/2001 | Andersen et al. |
| 6,174,331 | B1 | 1/2001 | Moe et al. |
| 6,183,512 | B1 | 2/2001 | Howanec et al. |
| 6,383,732 | B1 | 5/2002 | Stone |
| 6,461,382 | B1 | 10/2002 | Cao |
| 6,482,228 | B1 | 11/2002 | Norred |
| 6,558,418 | B2 | 5/2003 | Carpentier et al. |
| 6,761,735 | B2 | 7/2004 | Eberhardt et al. |
| 6,767,362 | B2 | 7/2004 | Schreck |
| 7,044,966 | B2 * | 5/2006 | Svanidze et al. ............. 623/2.1 |
| 7,172,625 | B2 | 2/2007 | Shu et al. |
| 7,247,167 | B2 * | 7/2007 | Gabbay ..................... 623/2.14 |
| 7,323,010 | B2 | 1/2008 | Verona et al. |
| 7,399,315 | B2 * | 7/2008 | Iobbi ......................... 623/1.26 |
| 7,556,645 | B2 * | 7/2009 | Lashinski et al. ............ 623/2.1 |
| 7,618,447 | B2 * | 11/2009 | Case et al. ................. 623/1.26 |
| 2001/0039450 | A1 | 11/2001 | Pavcnik et al. |
| 2003/0023302 | A1 | 1/2003 | Moe et al. |
| 2004/0098098 | A1 | 5/2004 | McGuckin et al. |
| 2005/0075724 | A1 * | 4/2005 | Svanidze et al. ........... 623/2.11 |
| 2005/0075726 | A1 * | 4/2005 | Svanidze et al. ........... 623/2.14 |
| 2006/0184239 | A1 | 8/2006 | Andrieu et al. |
| 2007/0288087 | A1 * | 12/2007 | Fearnot et al. ............. 623/1.24 |
| 2008/0133005 | A1 | 6/2008 | Andrieu et al. |
| 2008/0243246 | A1 * | 10/2008 | Ryan et al. ................. 623/2.18 |

FOREIGN PATENT DOCUMENTS

| | | |
|---|---|---|
| WO | WO 96/40008 A1 | 12/1996 |
| WO | WO 0067661 A | 11/2000 |
| WO | WO 01/30275 A | 5/2001 |
| WO | WO 2006/092648 A1 | 9/2006 |
| WO | WO 2008/035337 A2 | 3/2008 |
| WO | WO 2008/150529 A1 | 12/2008 |

OTHER PUBLICATIONS

International Search Report for International Application No. PCT/IB2005/000573, dated Dec. 14, 2005.
Office Action in U.S. Appl. No. 10/550,297, dated Apr. 19, 2007.
Final Office Action in U.S. Appl. No. 10/550,297, dated Nov. 20, 2007.
Office Action in U.S. Appl. No. 10/550,297 dated Apr. 17, 2008.
Amendment filed on Jul. 18, 2007 in Response to Office Action dated Apr. 19, 2007 in U.S. Appl. No. 10/550,297, filed Sep. 21, 2005.
Notice of Non-Compliant Amendment dated Jul. 27, 2007 in U.S. Appl. No. 10/550,297, filed Sep. 21, 2005.
Response filed on Aug. 8, 2007 to Notice of Non-Compliant Amendment dated Jul. 27, 2007 in U.S. Appl. No. 10/550,297, filed Sep. 21, 2005.
Supplemental Response filed on Aug. 27, 2007 to Notice of Non-Compliant Amendment dated Jul. 27, 2007 in U.S. Appl. No. 10/550,297, filed Sep. 21, 2005.
Interview Summary dated Jan. 31, 2008 in U.S. Appl. No. 10/550,297, filed Sep. 21, 2005.
Amendment Accompanying Request for Continued Examination dated Feb. 19, 2008 in Response to the Final Office Action dated Nov. 20, 2007 in U.S. Appl. No. 10/550,297, filed Sep. 21, 2009.
Amendment filed on Jul. 16, 2008 in response to Office Action dated Apr. 17, 2008 in U.S. Appl. No. 10/550,297, filed Sep. 21, 2005.
Final Office Action dated Oct. 30, 2008 in U.S. Appl. No. 10/550,297, filed Sep. 21, 2005.
Response filed on Dec. 29, 2008 to Final Office Action dated Oct. 30, 2008 in U.S. Appl. No. 10/550,297, filed Sep. 21, 2005.
Final Office Action dated Jan. 28, 2009 in U.S. Appl. No. 10/550,297, filed Sep. 21, 2005.
Response filed on Mar. 30, 2009 to Final Office Action dated Jan. 28, 2009 in U.S. Appl. No. 10/550,297, filed Sep. 21, 2005.
Interview Summary dated Apr. 2, 2009 in U.S. Appl. No. 10/550,297, filed Sep. 21, 2005.
Office Action dated Apr. 13, 2009 in U.S. Appl. No. 10/550,297, filed Sep. 21, 2005.
Interview Summary dated Jul. 7, 2009 in U.S. Appl. No. 10/550,297, filed Sep. 21, 2005.
Response filed on Jul. 13, 2009 to Office Action dated Apr. 13, 2009 in U.S. Appl. No. 10/550,297, filed Sep. 21, 2005.
Office Action dated Jun. 16, 2009 in U.S. Appl. No. 11/814,155, filed Jul. 17, 2007.
Office Action dated Dec. 9, 2009 in U.S. Appl. No. 10/550,297, filed Sep. 21, 2005.
Interview Summary dated Oct. 23, 2009 in U.S. Appl. No. 11/814,155, filed Jul. 17, 2007.
Partial International Search Report dated Feb. 11, 2010 in International Application No. PCT/US/2008/069344.
Final Office Action dated Feb. 17, 2010 in U.S. Appl. No. 11/814,155, filed Jul. 17, 2007.
Interview Summary dated May 5, 2010 in U.S. Appl. No. 10/550,297, filed Sep. 21, 2005.

* cited by examiner

REINFORCEMENT DEVICE FOR A BIOLOGICAL VALVE AND REINFORCED BIOLOGICAL VALVE

BACKGROUND OF THE INVENTION

1. Field of the Invention

This application generally relates to biological valve reinforcement devices, and, more particularly, to unstented biological heart valve reinforcement devices.

2. Description of the Related Art

Cardiac surgery often involves replacement of the patient's native valve with either a mechanical or biological (e.g., porcine, bovine, or homograft) valve.

A mechanical valvular prosthesis consists essentially of a mechanical valve device, such as a metal ball-and-cage or carbon bileaflet valve device, placed inside a ring covered by synthetic fabric. The ring facilitates incorporation of the device into the periphery of the orifice receiving the device. While mechanical prostheses have extremely long service lives, they present a significant clotting (thrombosis) risk and thus require the patient to undergo lifelong anticoagulation therapy. Furthermore, when mechanical valves do fail, the failure is likely to be catastrophic.

Biological valvular prostheses, on the other hand, comprise biological tissue taken from animals and treated by a suitable process so as to prepare them for implantation in the human body. Examples of biological valves include porcine aortic and mitral valves, porcine pulmonary valves, and aortic and mitral tissue valves that are reconstructed from a bovine pericardium. These valves have the advantage of a lower incidence of thrombosis, and thus minimize the need for prolonged anticoagulation therapy. Biological replacement valves further reduce the risk of catastrophic failure, as any problems that may occur tend to manifest symptomatically.

Biological valvular prostheses may either be stented or unstented. A stented valve comprises a biological tissue valve mounted on a metal or plastic frame (stent) which is covered by synthetic cloth. A stented design facilitates implantation of the biological prosthesis in that it requires only a single level of suture around its annular periphery. The tissue valve's position and configuration within the valve seat are maintained by the stent. An unstented biological valvular prosthesis, on the other hand, is not mounted on an external frame, but may be provided with synthetic cloth around the inflow opening. Implantation of unstented valves requires a more exacting surgical procedure than implantation of stented valves, due at least in part to the fact that unstented valves require more complex suturing in order to preserve the valve configuration once implanted. Furthermore, due to the geometry of the heart, unstented valves are generally restricted to use in the aortic position and are thus of limited application.

SUMMARY OF THE INVENTION

In accordance with one embodiment, a reinforcement device comprising a plurality of commissural supports, a plurality of intercommissural supports, and a base is described. Each commissural support is configured to stabilize a valve wall of a biological valve at a commissure of the biological valve. Each intercommissural support is configured to stabilize the valve wall at a location circumferentially between two of the commissures. The base is attached to the plurality of commissural supports and the plurality of intercommissural supports, and is configured to receive the biological valve mounted thereon at an inflow region of the biological valve. In one aspect of this embodiment, the commissural supports are configured to stand substantially within the valve wall. In the preceding aspect, the intercommissural supports may also be configured to stand substantially within the valve wall. In a further aspect, the commissural supports are configured to stand outside the valve wall. In the preceding aspect, the commissural supports may be configured to be sutured to the valve wall. In another aspect, the base is continuous around the valve wall in the inflow region of the biological valve. In another aspect, the commissural supports and intercommissural supports are discontinuous around the valve wall in an outflow region of the biological valve. In yet another aspect, the commissural supports and intercommissural supports are disposed at discrete locations of the valve wall in the outflow region of the biological valve. In another aspect, the commissural supports and the intercommissural supports comprise metal wire. The metal wire may comprise titanium. In another aspect, each of the commissural supports comprises first and second straight portions. The first and second straight portions may be spaced apart by a distance sufficient to avoid damaging a marking zone near the commissure when the commissural support is affixed to the valve wall. The first and second straight portions may be substantially parallel. Further, the first and second straight portions may be joined together by a curved portion. The curved portion may have a constant radius of curvature equal to half the distance between the first and second straight portions. The first and second straight portions may be configured to stand within the wall of the biological valve. The curved portion may be configured to stand at least partially outside the wall of the biological valve. In another aspect of the embodiment, each of the intercommissural supports comprises substantially parallel first and second straight portions. The first and second straight portions may be joined together by a curved portion. In yet another aspect, the plurality of commissural supports includes three commissural supports disposed generally symmetrically about the base. In a further aspect, the plurality of commissural supports includes three commissural supports disposed asymmetrically about the base. In the preceding aspect, the plurality of intercommissural supports may include three intercommissural supports, each one disposed between a pair of commissural supports. Each intercommissural support may be disposed approximately midway between each pair of commissural supports. In another aspect, the base comprises a ring and a cover. In the preceding aspect, the ring may be as thick or thicker than the valve wall. In another aspect, the base includes a first plurality of holes configured to closely receive the commissural supports and a second plurality of holes configured to closely receive the intercommissural supports. The first plurality may comprise five holes for each commissural support, for adjustable placement of the commissural supports with respect to the base. In a further aspect, the reinforcement device comprises a crimping wall configured to secure the commissural supports and intercommissural supports to the base when the crimping wall is pressed against the supports. In another aspect, the base comprises metal. The metal may comprise titanium. In these and other aspects, the biological valve may be an aortic or mitral valve.

In another embodiment, a reinforced prosthetic valve is described. This reinforced prosthetic valve comprises a biological valve mounted on a base, a plurality of commissural supports extending from the base, and a plurality of intercommissural supports extending from the base. The biological valve has leaflets attached to an external wall at commissures, and has an inflow and an outflow region. Each commissural support is configured to stabilize the external wall at one of the commissures. Each intercommissural support is configured to stabilize the external wall at a location circumferentially between two of the commissures. In one aspect of this embodiment, the commissural supports and intercommissural supports do not continuously surround the valve in the outflow region. In a further aspect, the commissural supports and the intercommissural supports are disposed substantially within the external wall. In another aspect, the commissural supports and the intercommissural supports are disposed outside the external wall. In the preceding aspect, the commissural supports and the intercommissural supports may be secured to the external wall with sutures.

In another embodiment, a method of reinforcing a biological valve is described. The biological valve has leaflets attached to an external wall at commissures. The method comprises securing a commissural support to the external wall at or near each commissure and coupling the commissural supports to a base. The method also comprises securing an intercommissural support to the external wall between each pair of commissural supports and coupling the intercommissural supports to a base. In one aspect of this embodiment the securing of the commissural supports to the external wall comprises inserting the commissural supports into the external wall in a generally longitudinal direction. In a further aspect, the securing of the commissural supports to the external wall comprises suturing the commissural supports to the external wall. In another aspect of the embodiment, the method further comprises the step of adjusting tension in the biological valve by adjusting the location of the commissural supports with respect to the base. In yet another aspect, the base is provided with a first plurality of holes configured to receive the commissural supports and a second plurality of holes configured to receive the intercommissural supports. The first plurality of holes may include five holes configured to allow adjustable placement of the commissural supports. The coupling of the commissural supports and intercommissural supports to the base may comprise crimping the commissural supports and intercommissural supports to the base.

In a further embodiment, a method of making a reinforced biological valve is described. A biological valve is provided which has a valve wall and a plurality of commissures. The biological valve comprises biological tissue that has been fixed in a physically unconstrained state. The method comprises securing a commissural support to the valve wall near each commissure and securing an intercommissural support to the valve wall between each pair of commissural supports. In one aspect of this embodiment, the method further comprises providing a base configured to couple with the commissural supports and intercommissural supports and adjusting tension in the biological valve by adjusting the location of the commissural supports with respect to the base. The biological valve may have an inflow region and an outflow region, and the commissural and intercommissural supports may be discontinuous around the valve in the outflow region. The commissural supports may be secured to the valve wall by inserting them, longitudinally, into the valve wall.

Yet another embodiment is a method of making a reinforced biological valve. The biological valve has a valve wall, a plurality of commissures, an inflow region, and an outflow region. The method comprises fixing biological tissue in a physically unconstrained state, forming a biological valve from the biological tissue, attaching a commissural support to the valve wall near each commissure, and attaching an intercommissural support to the valve wall between each pair of commissural supports. In one aspect of this embodiment, the commissural and intercommissural supports do not continuously surround the biological valve in the outflow region. The commissural supports may be attached to the valve wall by placing them substantially within the valve wall.

Still another embodiment is a method of replacing a malfunctioning valve in a subject. The method comprises removing the malfunctioning valve from the subject, providing a reinforced biological valve comprising a plurality of commissural supports and a plurality of intercommissural supports, and implanting the reinforced biological valve in the subject in place of the malfunctioning valve. Each commissural support is configured to stabilize a commissure of the biological valve and each intercommissural support is configured to stabilize a wall of the biological valve between each pair of commissural supports. The commissural supports and intercommissural supports are disposed at discrete locations about an outflow region of the biological valve.

DETAILED DESCRIPTION OF CERTAIN INVENTIVE ASPECTS

Figure 1:
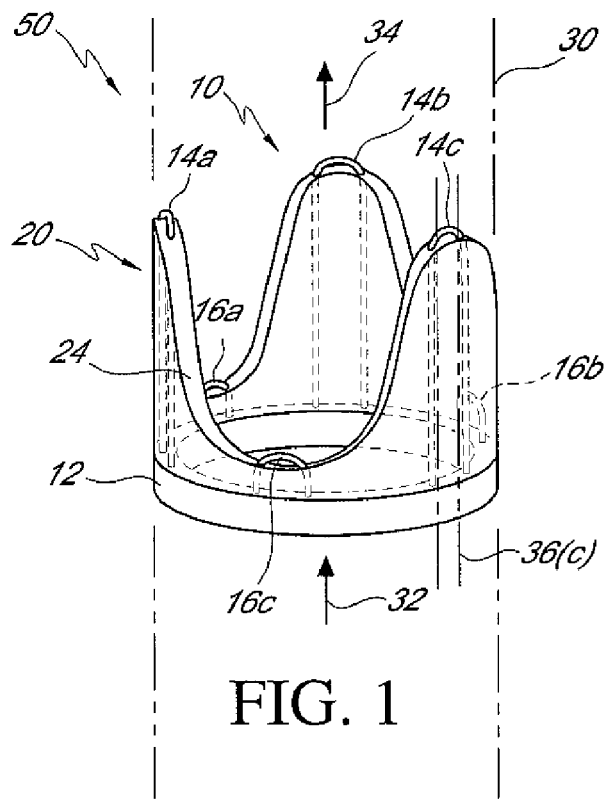
FIG. 1 is a perspective representation of a reinforcement device according to an embodiment, placed within the walls of a biological tissue valve (valve leaflets not shown).

The features, aspects and advantages of the present invention will now be described with reference to the drawings of several embodiments, which are intended to be within the scope of the invention herein disclosed. These and other embodiments will become readily apparent to those skilled in the art from the following detailed description of the embodiments having reference to the attached figures, the invention not being limited to any particular embodiment(s) disclosed.

As mentioned in the Background section, stented valves comprise an external frame (stent) on which a biological tissue valve is mounted. The stent continuously surrounds and supports the outflow region of the valve (the region beyond the leaflet plane, in the direction of flow) to hold the valve wall in an open configuration. While stented valves offer relative ease of implantation and configurational stability after implantation, stented designs also add bulk to a replacement valve device. Stented designs can result in a significant (on the order of 3-8 mm) reduction in the diameter of the ventricular outflow tract, thereby artificially increasing the pressure gradient in the valve. Stented designs can also decrease the effective orifice area (EOA) of a valve. Stented designs may thus offer relatively poor hemodynamics as compared with unstented designs.

Because unstented valves introduce little or no added bulk, the pressure gradient in the replacement valve more closely resembles the natural value. Unstented designs can also offer increased flexibility over stented designs. Unstented designs thus offer an advantage in terms of hemodynamics. Conventional unstented designs, however, are more difficult to orient during implantation and require more complex suturing in order to preserve the valve configuration after implantation. This undesirably leads to longer surgery times and adds both risk and expense to procedures. Furthermore, complex intraoperative suturing can alter the intended geometry of the valve.

Another disadvantage of conventional biological replacement valve designs is that, in order to establish the root geometry, they require some artificial external stress (axial, radial, and/or circumferential) to be placed on the valve leaflets during the crosslinking (fixation) process. This undesirably affects both the biomechanical properties of the leaflet tissue and the anatomical configuration of the leaflets with respect to each other, because the tissue is effectively fixed in a somewhat pre-stressed state. This diminishes the leaflets' ability to function normally and negatively impacts the valve's performance characteristics. Conventional methods also compensate for tissue shrinkage—which tends to occur during fixation—by starting (pre-fixation) with an oversized valve. Post-fixation, this results in extra tissue bulk, reducing the EOA of conventional reinforced valves.

Various embodiments of the invention advantageously provide a device for and method of supporting and stabilizing a biological heart valve without adding significant bulk or reducing the operative diameter of the valve. Embodiments thus allow for replacement of a native valve with an optimally-sized prosthesis. Embodiments of the invention additionally provide a reinforced prosthetic valve which may be prepared in advance of surgery and installed in a relatively quick and simple manner, without the need for complex suturing during implantation. Certain reinforced prosthetic valves are described in U.S. patent application Ser. No. 10/550,297 entitled "Intraparietal Aortic Valve Reinforcement Device and Reinforced Aortic Valve," and PCT Application No. PCT/IB2005/000573 entitled "A Reinforcing Intraparietal Device for a Biological Cardiac Prosthesis and a Reinforced Biological Cardiac Prosthesis," the disclosures of which are incorporated by reference herein in their entireties.

Additionally, the commissural and intercommissural supports used in these and other embodiments can provide points of reference for the surgeon, aiding the surgeon in marking the proper orientation of a prosthesis and facilitating its implantation. Thus, these and other embodiments combine the advantages of conventional stented and unstented valves, while reducing or eliminating their related disadvantages.

Embodiments also desirably allow for the reestablishment of the natural heart valve root configuration—which will be further described below as a "double-trigone" geometry—without the need for mechanical, hydrostatic, or other external stabilization means during crosslinking. Instead, the biological tissue may be fixed in a zero-stress environment, without affecting the morphology of the collagen or elastin of the tissue, thereby fixing the tissue in a natural, unstressed state. The root geometry may then be re-established (and manipulated if necessary) post-fixation, using supports placed close to or inside the valve walls at the commissures and in the intercommissural spaces. Stabilizing the valve wall at discrete locations, discontinuously about the outflow region, reinforces the root geometry while allowing some flexibility in the non-reinforced portions of the valve wall during operation of the valve.

Furthermore, as mentioned above, the fixation process may cause a certain amount of shrinkage in the biological tissue. Providing zero-stress fixation, according to embodiments of the invention, allows for optimal sizing of the valve tissue with a reinforcement device, because the slightly shrunken (fixed) tissue can be stretched back to approximately its original size post-fixation. This reduces or eliminates undesirable added tissue bulk, increasing the EOA of the valve as compared to conventional configurations. Providing zero-stress fixation also minimizes the introduction of undesirable artificial stresses on the valve leaflets during operation of the valve. Embodiments thus require less work to open the leaflets, minimizing energy loss across a reinforced valve.

A Reinforced Valve

With reference now to FIG. 1, an embodiment of a reinforced biological valve 50 is illustrated. The reinforced valve 50 includes a biological valve reinforcement device 10 having commissural supports 14(a)-14(c) and intercommissural supports 16(a)-16(c) disposed largely within an external wall 24 of a biological valve 20 (the valve leaflets are not shown in FIG. 1). Alternatively, the device 10 may include commissural and intercommissural supports disposed just outside the valve 20 and secured to the valve tissue, for example by suturing. As better illustrated in FIG. 3, the biological valve 20 includes three leaflets 22(a)-26(c) attached laterally to the external wall 24 at three commissures 26(a)-26(c). At the intersection of each of the commissures 26(a)-26(c) with the wall 24 is a "marking zone" having a complex fortified anatomy. The marking zone 36(c), corresponding to commissure 26(c), is illustrated in dashed lines. A native channel 30 into which the reinforced valve 50 may be implanted is also illustrated with dashed lines. The native channel 30 may, for example, be an aortic channel. The direction of flow through the valve 20 is indicated by arrows 32 (inflow) and 34 (outflow).

A Reinforcement Device

In the embodiment illustrated in FIG. 1, the device 10 generally includes a base 12 (upon which the biological valve 20 may be mounted), a plurality of commissural supports 14(a)-14(c) (shown largely in hidden lines), and a plurality of intercommissural supports 16(a)-16(c) (also shown largely in hidden lines). The commissural supports 14(a)-14(c) may be disposed generally at the commissures of the valve 20, and the intercommissural supports 16(a)-16(c) may be disposed in or near the valve wall 24. In some embodiments the intercommissural supports 16(a)-16(c) are positioned approximately midway between each pair of commissures. However, it will be appreciated that the intercommissural supports may be positioned anywhere consistent with their intended function. Both the commissural and intercommissural supports 14(a)-14(c) and 16(a)-16(c) may be coupled to the base 12.

Base

With continued reference to FIG. 1, the base 12 may have an internal diameter which is substantially equivalent to an internal diameter of the biological valve 20. Thus, the inflow region of the valve 20 (the region before the leaflet plane, moving in the direction of flow) may be mounted directly on top of the base 12, as shown in the figure, with the inner wall of the valve 20 being essentially flush with the inner surface of the base 12. The base 12 may further have a thickness which may preferably be substantially equivalent to a thickness of the wall 24 of the biological valve 20. Accordingly, the base 12 may have an external diameter which may preferably be substantially equivalent to an external diameter of the wall 24 of the biological valve 20. The thickness of the base 12 may also be greater than or smaller than the thickness of the biological valve 20. With a smaller sized valve, for example, the base 12 may have a thickness slightly larger than the thickness of the valve wall.

Figure 2:
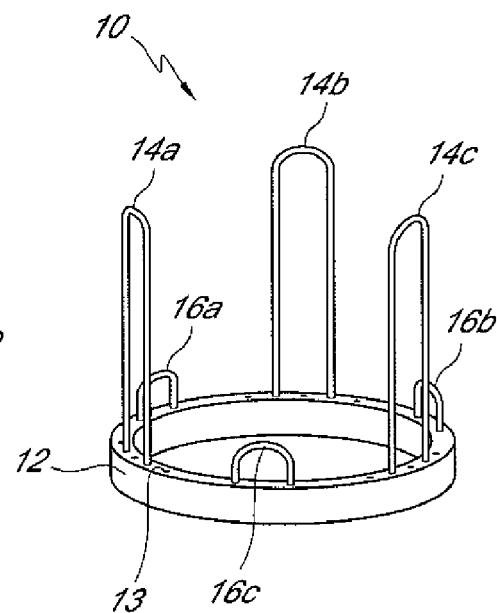
FIG. 2 is a perspective representation of the intramural reinforcement device of FIG. 1.
Figure 7:
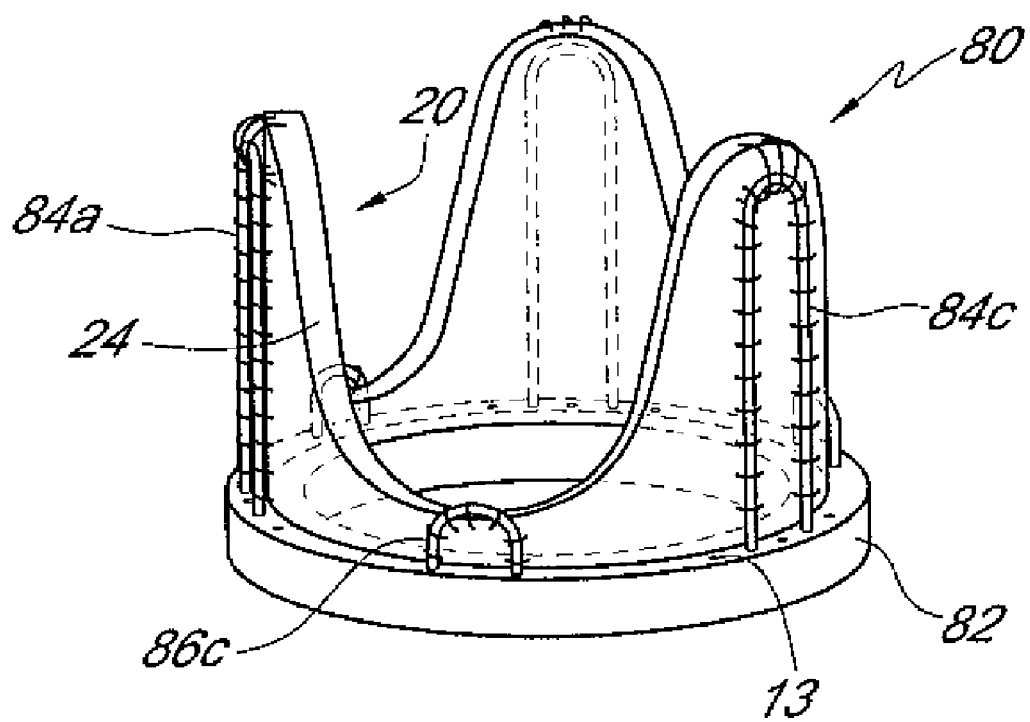
FIG. 7 is a perspective representation of a reinforcement device according to an alternative embodiment (valve leaflets not shown).

As shown in FIG. 2, the base 12 may be provided with a plurality of holes 13. The holes 13 may be disposed on the top surface of the base 12 midway between the inner and outer walls of the base 12 (as shown in FIG. 2) or at the outer edge of the top surface of the base (see FIG. 7). The holes 13 may also be disposed at any other position consistent with their intended use. The holes 13 may be configured to receive the commissural and intercommissural supports 14(a)-14(c) and 16(a)-16(c) (which will be described in further detail below).

Figure 5A:
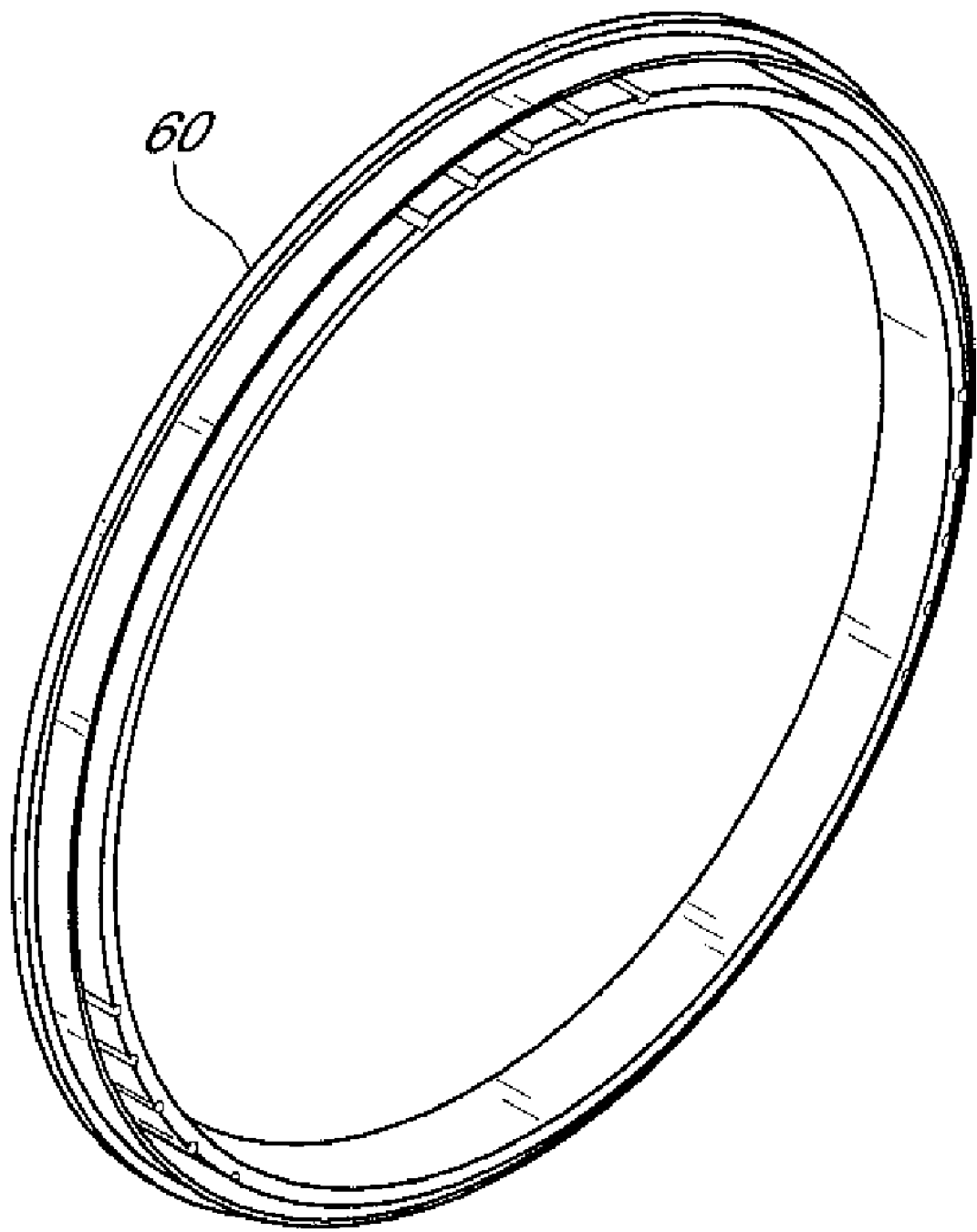
FIG. 5A is a perspective view of a ring portion of a base according to an embodiment.
Figure 5B:
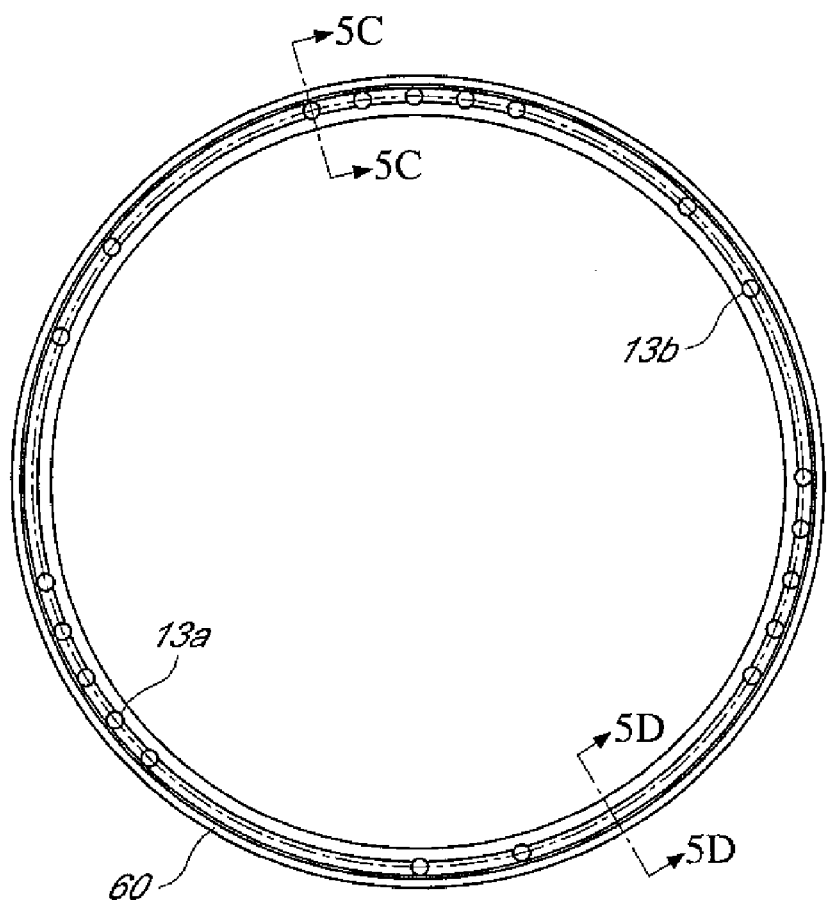
FIG. 5B is a bottom plan view of the ring of FIG. 5A.

As better illustrated in FIGS. 5A-5B, one or more holes 13(a) may be provided for each commissural support 14(a)-14(c) to allow for adjustable placement of the commissural supports 14(a)-14(c) around the base 12. For example, if the supports 14(a)-14(c) have legs spaced 4 mm apart, five holes may be provided and spaced 2 mm apart so that a support may fit in the first and third holes, the second and fourth holes, or the third and fifth holes. The holes 13(a) or sets of holes 13(a) may be disposed somewhat asymmetrically around the base 12; for example, in some embodiments, they may be spaced approximately 120°, 105°, and 135° from each other. The holes 13(a) or sets of holes 13(a) may alternatively be disposed generally symmetrically around the base 12, depending upon the requirements of the particular application.

Additionally, one or more holes 13(b) may be provided for each intercommissural support 16(a)-16(c). As illustrated in FIG. 5B, each hole 13(b) or set of holes 13(b) may be disposed approximately midway between each set of commissural support holes 13(a). Of course, the commissural support holes 13(a) and the intercommissural support holes 13(b) may be disposed in any other configuration consistent with their intended use. For example, the base 12 may be provided with evenly spaced holes 13 to allow for maximum adjustability, or may be provided with holes 13 located in discrete positions to ensure precise positioning of the supports 14(a)-14(c) and 16(a)-16(c).

Figure 5C:
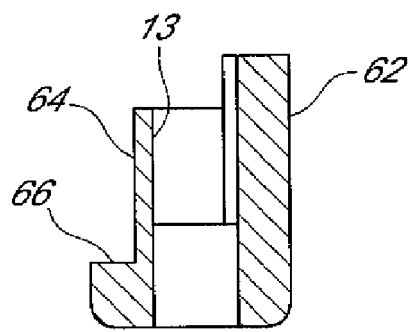
FIG. 5C is a cross-sectional view of the ring shown in FIG. 5A taken along line 5C-5C of FIG. 5B.
Figure 5D:
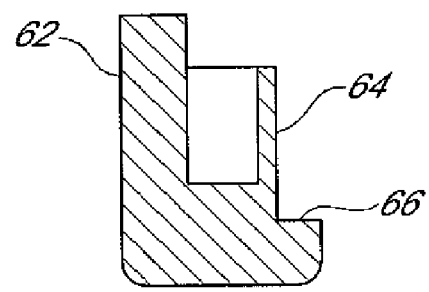
FIG. 5D is a cross-sectional view of the ring shown in FIG. 5A taken along line 5D-5D of FIG. 5B.
Figure 6A:
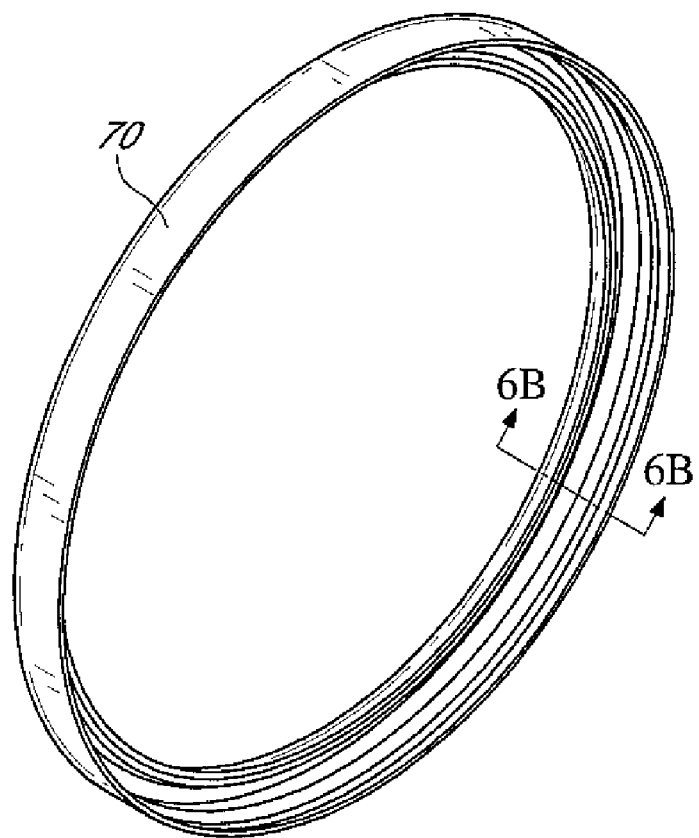
FIG. 6A is a perspective view of a cover portion of a base according to an embodiment.
Figure 6B:
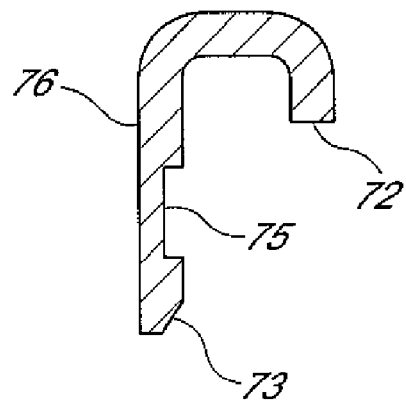
FIG. 6B is a cross-sectional view of the cover of FIG. 6A taken along line 6B-6B of FIG. 6A.

With reference now to FIGS. 5A-5D and 6A-6B, in some embodiments, the base 12 may comprise a ring 60 and a cover 70. The ring 60 may be provided with a plurality of holes 13 as described above. As shown in FIGS. 5C-5D, the ring 60 may have an inner wall 62, a crimping wall 64, and an outer lip 66. The crimping wall 64 may be configured to provide a friction crimp against a support 14, 16 inserted into one of the holes 13 when the wall 64 is pressed against the support 14, 16. As shown in FIGS. 6A-6B, the cover 70 may have an inner lip 72, configured to mate with the inner wall 62 of the ring 60, and an outer wall 76, configured to mate with the outer wall 66 of the ring 60. The outer wall 76 may be provided with a chamfer 73 configured to allow the cover 70 to slip over the crimped surfaces of the crimping wall 64 of the ring 60. The outer wall 76 may further be provided with an annular groove 75 configured to clip to the crimped surfaces of the crimping wall 64. In alternative embodiments, the base 12 may have any other configuration allowing it to secure the supports 14, 16 and to support a biological valve mounted thereon.

The base 12 may comprise any suitable material for receiving and/or securing the supports 14(a)-14(c) and 16(a)-16(c). For example, the base 12 may be formed from a metal such as titanium. Alternatively, the base 12 may be formed from a rigid, semi-rigid, or flexible polymer.

Commissural Supports

Figure 3:
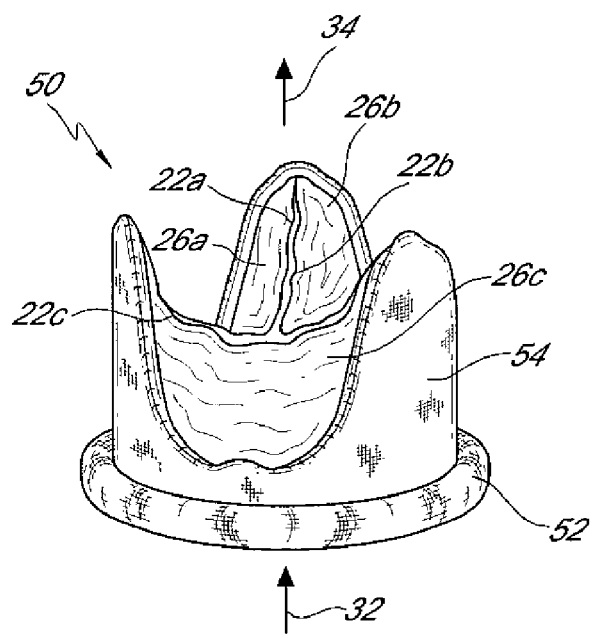
FIG. 3 is a perspective drawing of a reinforced biological valve according to a further embodiment and showing the direction of flow through the valve.

Referring once again to the embodiment depicted in FIG. 2, the commissural supports 14(a)-14(c) may be disposed at each of the commissures 26 and coupled to the base 12. The commissural supports 14(a)-14(c) may each comprise two legs connected by a curvilinear portion at an end of the support distal of the base 12. The two legs may be generally straight and generally parallel (as illustrated in the figure) or may be curved or angled apart somewhat. The two legs may also be spaced apart by a distance sufficient to avoid damaging the biological tissue in the marking zones 36(a)-36(c) (marking zone 36(c) is illustrated in FIG. 3) of the biological valve 20, thereby preserving the structural integrity of the biological valve 20. For example, the legs may be separated by a distance of 4 mm, or 3 mm (especially in the case of smaller-sized valves). The legs may also be separated by any distance compatible with the valve's intended use. In some embodiments, the curvilinear portion may have a constant radius of curvature, which may be equivalent to half the distance between the parallel legs.

In the embodiment shown in FIG. 1, the commissural supports 14(a)-14(c) may be configured to stand largely within the external wall 24 of the biological valve 20. Alternative embodiments may include commissural supports having any configuration capable of providing adequate support to the commissures during exposure to physiological flow pressures and rates. For example, the embodiment illustrated in FIG. 7 has commissural supports 84(a)-84(c) disposed external to the valve wall 24 around the outer periphery of a base 82, the valve 20 being disposed on top of the base 82 and having its inner wall essentially flush with the inner periphery of the base 82. An external commissural support may comprise a single straight rod, a T-shaped rod, a curved wire, or a narrow blade or plate which may be sutured to or otherwise attached to biological valve tissue at the valve commissures (see FIG. 7). Depending upon the geometry of the biological valve 20, the commissural supports may be disposed somewhat asymmetrically around the base, as described above in connection with FIGS. 5A-5B. The commissural supports may also be disposed about the base in any other configuration consistent with their intended use.

Referring again to the embodiment depicted in FIG. 1, the commissural supports 14(a)-14(c) may be disposed in a direction substantially parallel to the direction of flow 32 through the valve 20. The legs of the commissural supports 14(a)-14(c) may be disposed entirely within the tissue of the wall 24, while the curvilinear portions of the commissural supports 14(a)-14(c) may extend partially or entirely outside of the tissue at an end distal of the base 12. The commissural supports 14(a)-14(c) may each comprise a continuous wire, such as a titanium wire, for example. Alternatively, the commissural supports 14(a)-14(c) may comprise a rigid, semi-rigid, or flexible polymer.

Figure 4:
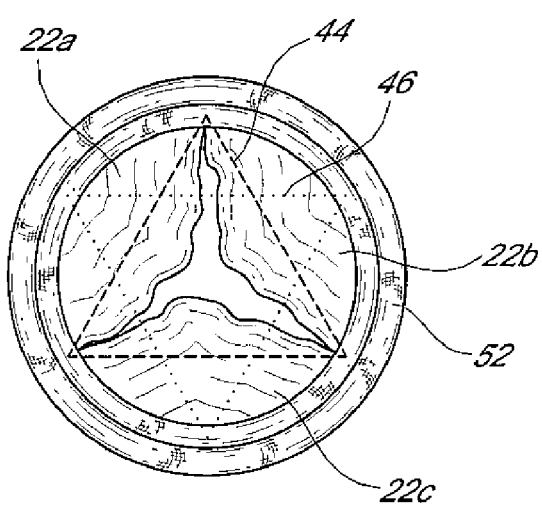
FIG. 4 is a bottom plan view of the reinforced biological valve of FIG. 3, showing the valve inflow and illustrating the commissural and intercommissural trigone geometries.

With reference now to the embodiment depicted in FIG. 4, which illustrates a bottom plan view of the device 10 incorporated into the reinforced biological valve 50, the commissural supports 14(a)-14(c) may together define a commissural trigone 44 (shown in dashed lines).

Intercommissural Supports

Referring once again to the embodiment depicted in FIG. 1, the intercommissural supports 16(a)-16(c) (shown largely in hidden lines) may be disposed in the intercommissural spaces, preferably approximately midway between each pair of commissural supports 14(a), 14(b); 14(b), 14(c); and 14(c), 14(a). The intercommissural supports 16(a)-16(c) may also be coupled to the base 12. In the embodiment in FIG. 1, the intercommissural supports 16(a)-16(c) may be configured to stand largely within the external wall 24 of the biological valve 20. Alternative embodiments may include intercommissural supports disposed externally to the biological valve tissue, which supports may be sutured or otherwise attached to the valve tissue in the intercommissural spaces (see FIG. 7).

Referring again to the embodiment depicted in FIG. 2, the intercommissural supports 16(a)-16(c) may each comprise two legs connected by a curvilinear portion at an end of the support distal of the base 12. The two legs may be generally straight and generally parallel (as illustrated in the figure) or may be curved or angled apart somewhat. The curvilinear portion may have a constant radius of curvature equivalent to half the distance between the parallel legs. Alternatively, because the intercommissural spaces include no especially fragile marking zones, the intercommissural supports may each comprise a single straight rod, a T-shaped rod, or a narrow blade or plate. Embodiments may include intercommissural supports having other shapes, such as helical shapes, which may aid in insertion of the support into the valve tissue.

In the embodiment depicted in FIG. 1, the intercommissural supports 16(a)-16(c) may be disposed in a direction substantially parallel to the direction of flow 32. The legs of the intercommissural supports 16(a)-16(c) may be disposed entirely within the tissue of the wall 24, while the curvilinear portions of the intercommissural supports 16(a)-16(c) may extend partially or entirely outside of the tissue at an end distal of the base 12. In the embodiment depicted in FIG. 2, because the wall 24 is typically cut shorter in the intercommissural spaces than near the commissures 26, the intercommissural supports 16(a)-16(c) may be shorter than the commissural supports 14(a)-14(c). The intercommissural supports 16(a)-16(c) may each comprise a continuous wire, such as a titanium wire, for example. Alternatively, the intercommissural supports 16(a)-16(c) may comprise a rigid, semi-rigid, or flexible polymer.

Referring once again to FIG. 4, the intercommissural supports 16(a)-16(c) may together define an intercommissural trigone 46 (shown in dashed lines). The intercommissural trigone configuration 46 may serve to resist radial forces on the intercommissural spaces when the valve leaflets 22 close. Thus, the commissural supports 14(a)-14(c) and intercommissural supports 16(a)-16(c) together define a double-trigone geometry (see lines 44, 46) which closely resembles the natural geometry of the biological valve 20.

Referring now to FIG. 3, the reinforced biological valve 50 may be provided with a suture ring 52, which may comprise a flexible synthetic fabric. The entire outside periphery of the valve 50 may also be covered by a synthetic fabric 54.

Making a Reinforcement Device and a Reinforced Valve

A method of reinforcing a biological valve is also provided. The method may include placing a commissural support at or near each commissure of a biological valve and securing the commissural supports to the valve tissue. The method may also include placing an intercommissural support approximately midway between each pair of commissural supports and securing the intercommissural supports to the valve tissue. The method may further include coupling the commissural supports and intercommissural supports to a base, which may be disposed underneath the biological valve.

In some embodiments, after biological material to be used for the replacement valve is first harvested, it may be stored in a preservative solution. The biological material may then be subjected to one or more pre-fixation treatments, such as a decellularization treatment to reduce the risk of post-implantation mineralization. Such pre-fixation treatments are more fully described in U.S. Pat. Nos. 5,595,571; 5,720,777; and 5,843,181; the entire disclosures of which are herein incorporated by reference.

The biological material may then be subjected to a fixation (crosslinking) treatment to preserve the structural integrity of the biological valve. Such fixation may include exposing the biological material to gluteraldehyde. Such fixation may occur without any mechanical, hydrostatic, or other external stress placed on the valve leaflets. Fixing the biological tissue in a "relaxed" state allows for some shrinkage of the material to occur without affecting the orientation of collagen or elastin in the tissue, and thus without affecting the biomechanical properties of the tissue. The tissue may be then be dissected and composited into a composite biological valve, according to known practices. Embodiments of the invention may also use an intact biological valve.

Next, commissural supports may be inserted into the wall of the biological valve. Each commissural support may comprise two legs, each leg being provided with a sharp tip for piercing the wall of the tissue valve at either side of the commissural marking zone. The legs may have differing lengths to facilitate insertion. The legs may enter the valve wall at the outflow region of the valve and be pushed through the wall in a direction generally parallel to the central axis of the valve until the legs exit the tissue at the inflow region of the valve. Alternatively, the commissural supports may be placed outside the valve wall at each commissure and secured to the valve tissue in any suitable fashion, for example by suturing.

Once each commissural support is inserted through (or otherwise coupled to) the valve wall, the supports may be coupled to a base. The commissural supports may be removably coupled to the base at first, to allow a practitioner to choose a differently-sized base if necessary. In view of the size of the biological tissue, the commissural supports may also be adjustably positioned on the base to allow a practitioner to adjust the height of the supports and to adjust tension among the valve leaflets as necessary. As noted above, the valve tissue may have shrunken to a certain extent (on the order of one valve size, that is, approximately 2 mm in diameter) during the zero-stress fixation. Thus, the process of coupling the commissural supports to the base may involve stretching the valve tissue slightly to re-establish the original valve size.

After the proper sizing and positioning has been determined, the commissural supports may be more permanently fixed to the base to establish the commissural trigone. The commissural supports may be fixed by crimping a wall of the base against the legs of the supports. The supports may be fixed using a friction crimp, allowing adjustment of the height of supports, or may be fixed using a fixed crimp so that the supports become firmly positioned with respect to the base. The commissural supports may alternatively be fixed by any other manner consistent with the valve's intended use. Once the commissural supports are secured to the base, the supports may be bent at an approximately 90° angle (tangentially from the base) and trimmed.

After the commissural trigone has been established, the intercommissural supports may be inserted into the valve wall. Each intercommissural support may comprise one or more legs, each leg being provided with a sharp tip for piercing the wall of the tissue valve. The legs may enter the valve wall at the outflow region of the valve and be pushed through the wall until the legs exit the tissue wall at the inflow region of the valve. As with the commissural supports, the intercommissural supports may alternatively be placed outside the valve wall at each intercommissural space and secured to the valve tissue in any suitable fashion, for example by suturing. The intercommissural supports may then be coupled to the base and trimmed in a similar manner as the commissural supports. Where a base comprising a ring and a cover is used, a cover may then be placed on the ring and secured to the ring.

Finally, the reinforced valve may be covered or partially covered with a flexible synthetic fabric. The reinforced valve may also be encircled by a suture ring, such as a flexible fabric ring, which can be used to facilitate implantation of the device.

Using a Reinforced Valve

During an aortic valve replacement surgery, a diseased or malfunctioning native valve is removed from the native aortic annulus. The aortic annulus is then sized, and a pre-manufactured reinforced biological valve of the appropriate size is selected for implantation. As mentioned earlier, providing reinforcement of the double-trigone geometry for a biological valve allows for optimal sizing of the replacement valve, thereby maintaining a more natural pressure gradient and reducing or eliminating the need to perform root enlargement or other such procedures. The surgeon then sutures the replacement valve within the aortic annulus or supra-annularly, using the commissural reinforcement points as markers to properly orient the reinforced valve. Since the double-trigone geometry of the valve is reinforced at discrete locations around the circumference of the valve, no complex suturing is required to secure the valve's configuration.

Although the hemodynamic characteristics of bioprosthetic heart valves measured in flow testing have not been proven to be proportional to their in situ clinical performance, there is a general agreement that for a particular cardiac output, expressed as liters of blood passing through in any one minute, the degree to which the valve opens and the effort necessary to accomplish adequate flow during flow tests are most likely related to the clinical outcome. In flow tests, embodiments of the invention have demonstrated enhanced hemodynamics when compared with even the most hemodynamically efficient conventional bioprostheses. For example, flow testing has shown that a 25 mm diameter valve, configured in accordance with embodiments of the invention, has an approximately 20 to 25% greater EOA than a conventional stented bioprosthetic valve of the same size. An increased BOA results in more blood flow per heart beat, and also results in a lower total energy loss during valve operation. Thus, to accommodate a given cardiac output, the 25 mm valve mentioned above only requires about half the work as a conventional stented bioprosthetic valve of the same size. This indicates that, for aortic applications, the left ventricle of the heart will be required to perform less work, resulting in an accelerated return of normal function.

Although illustrated within the context of a prosthetic aortic valve, the present invention may also be used with other prosthetic valves, such as a mitral valve, tricuspid valve, or any other valve for which unobstructing reinforcement is desirable. It will be understood by those of skill in the art that numerous and various modifications can be made without departing from the spirit of the present invention. Therefore, it should be clearly understood that the forms of the invention described herein are illustrative only and are not intended to limit the scope of the invention.

What is claimed is:

1. A reinforcement device comprising:
 a plurality of commissural supports, each commissural support being configured to stabilize a valve wall of a biological valve at a commissure of the biological valve, the biological valve having an inflow region and an outflow region;
 a plurality of intercommissural supports, each intercommissural support being configured to stabilize the valve wall at a location circumferentially between two of the commissures; and
 a base disposed at the inflow region of the biological valve, the base being attached to the plurality of commissural supports and the plurality of intercommissural supports, the base further being configured to receive the biological valve mounted thereon, wherein the commissural supports and intercommissural supports are discontinuous around the valve wall in the outflow region of the biological valve.

2. The reinforcement device of claim 1, wherein the commissural supports are configured to stand substantially within the valve wall.

3. The reinforcement device of claim 2, wherein the intercommissural supports are configured to stand substantially within the valve wall.

4. The reinforcement device of claim 1, wherein the commissural supports are configured to stand outside the valve wall.

5. The reinforcement device of claim 4, wherein the commissural supports are configured to be sutured to a valve wall.

6. The reinforcement device of claim 1, wherein the base is continuous around the valve wall in the inflow region of the biological valve.

7. The reinforcement device of claim 1, wherein the commissural supports and intercommissural supports are disposed at discrete locations of the valve wall in the outflow region of the biological valve.

8. The reinforcement device of claim 1, wherein the commissural supports and the intercommissural supports comprise metal wire.

9. The reinforcement device of claim 8, wherein the metal wire comprises titanium.

10. The reinforcement device of claim 1, wherein each of the commissural supports comprises first and second straight portions.

11. The reinforcement device of claim 10, wherein the first and second straight portions are spaced apart by a distance sufficient to avoid damaging a marking zone near the commissure when the commissural support is affixed to the valve wall.

12. The reinforcement device of claim 11, wherein the first and second straight portions are substantially parallel.

13. The reinforcement device of claim 12, wherein the first and second straight portions are joined together by a curved portion.

14. The reinforcement device of claim 13, wherein the curved portion has a constant radius of curvature equal to half the distance between the first and second straight portions.

15. The reinforcement device of claim 10, wherein the first and second straight portions are configured to stand within the wall of the biological valve.

16. The reinforcement device of claim 13, wherein the curved portion is configured to stand at least partially outside the wall of the biological valve.

17. The reinforcement device of claim 1, wherein each of the intercommissural supports comprises substantially parallel first and second straight portions.

18. The reinforcement device of claim 16, wherein the first and second straight portions are joined together by a curved portion.

19. The reinforcement device of claim 1, wherein the plurality of commissural supports includes three commissural supports disposed generally symmetrically about the base.

20. The reinforcement device of claim 1, wherein the plurality of commissural supports includes three commissural supports disposed asymmetrically about the base.

21. The reinforcement device of claim 20, wherein the plurality of intercommissural supports includes three intercommissural supports, each one of the intercommissural supports being disposed between each pair of commissural supports.

22. The reinforcement device of claim 21, wherein each of the intercommissural supports is disposed approximately midway between each pair of commissural supports.

23. The reinforcement device of claim 1, wherein the base comprises a ring and a cover.

24. The reinforcement device of claim 23, wherein the ring has a thickness substantially equivalent to a thickness of the valve wall.

25. The reinforcement device of claim 23, wherein the ring has a thickness greater than a thickness of the valve wall.

26. The reinforcement device of claim 1, wherein the base includes a first plurality of holes configured to closely receive the commissural supports and a second plurality of holes configured to closely receive the intercommissural supports.

27. The reinforcement device of claim 26, wherein the first plurality comprises five holes for each commissural support for adjustable placement of the commissural supports with respect to the base.

28. A reinforcement device comprising:
a plurality of commissural supports, each commissural support being configured to stabilize a valve wall of a biological valve at a commissure of the biological valve, the biological valve having an inflow region and an outflow region;
a plurality of intercommissural supports, each intercommissural support being configured to stabilize the valve wall at a location circumferentially between two of the commissures;
a base disposed at the inflow region of the biological valve, the base being attached to the plurality of commissural supports and the plurality of intercommissural supports, the base further being configured to receive the biological valve mounted thereon, wherein the base includes a first plurality of holes configured to closely receive the commissural supports and a second plurality of holes configured to closely receive the intercommissural supports; and
a crimping wall configured to secure the commissural supports and intercommissural supports to the base when the crimping wall is pressed against the supports.

29. The reinforcement device of claim 1, wherein the base comprises metal.

30. The reinforcement device of claim 29, wherein the metal comprises titanium.

31. The reinforcement device of claim 1, wherein the biological valve is an aortic valve.

32. The reinforcement device of claim 1, wherein the biological valve is a mitral valve.

33. A reinforced prosthetic valve comprising:
a biological valve having leaflets attached to an external wall at commissures, the biological valve having an inflow region and an outflow region, the biological valve being mounted on a base;
a plurality of commissural supports extending from the base, each commissural support configured to stabilize the external wall at one of the commissures; and
a plurality of intercommissural supports extending from the base, each intercommissural support being configured to stabilize the external wall at a location circumferentially between two of the commissures, wherein the commissural supports and intercommissural supports do not continuously surround the valve in the outflow region.

34. The reinforced prosthetic valve of claim 33, wherein the commissural supports and the intercommissural supports are disposed substantially within the external wall.

35. The reinforced prosthetic device of claim 33, wherein the commissural supports and the intercommissural supports are disposed outside the external wall.

36. The reinforced prosthetic device of claim 35, wherein the commissural supports and the intercommissural supports are secured to the external wall with sutures.

* * * * *

UNITED STATES PATENT AND TRADEMARK OFFICE
CERTIFICATE OF CORRECTION

| | | |
|---|---|---|
| PATENT NO. | : 7,815,677 B2 | Page 1 of 1 |
| APPLICATION NO. | : 11/775043 | |
| DATED | : October 19, 2010 | |
| INVENTOR(S) | : Jaffe et al. | |

It is certified that error appears in the above-identified patent and that said Letters Patent is hereby corrected as shown below:

In Column 3, Line 21, after "embodiment", please insert --,--.

In Column 11, Line 44, please delete "BOA" and insert --EOA-- therefor.

Signed and Sealed this
Fifth Day of April, 2011

David J. Kappos
*Director of the United States Patent and Trademark Office*

(12) EX PARTE REEXAMINATION CERTIFICATE (9789th)
United States Patent
Jaffe et al.

(10) Number: US 7,815,677 C1
(45) Certificate Issued: Aug. 7, 2013

(54) REINFORCEMENT DEVICE FOR A BIOLOGICAL VALVE AND REINFORCED BIOLOGICAL VALVE

(75) Inventors: Norman Jaffe, Dana Point, CA (US); Afksendiyos Kalangos, Geneva (CH); Yuri Zhivilo, Moscow (RU)

(73) Assignee: Leman Cardiovascular SA, Lonay (CH)

Reexamination Request:
No. 90/012,549, Sep. 13, 2012

Reexamination Certificate for:
Patent No.: 7,815,677
Issued: Oct. 19, 2010
Appl. No.: 11/775,043
Filed: Jul. 9, 2007

Certificate of Correction issued Apr. 5, 2011

(51) Int. Cl.
*A61F 2/24* (2006.01)
(52) U.S. Cl.
USPC ................................................ 623/2.14

(58) Field of Classification Search
None
See application file for complete search history.

(56) References Cited

To view the complete listing of prior art documents cited during the proceeding for Reexamination Control Number 90/012,549, please refer to the USPTO's public Patent Application Information Retrieval (PAIR) system under the Display References tab.

*Primary Examiner* — Glenn K. Dawson

(57) ABSTRACT

A reinforcement device for a biological valve includes an arrangement of supports configured to establish a double-trigone geometry in the valve and coupled to a base upon which the valve may be mounted. A plurality of commissural supports establish the geometry of a commissural trigone, and a plurality of intercommissural supports establish the geometry of an intercommissural trigone. A method for reinforcing a biological valve includes using commissural supports in conjunction with intercommissural supports, both sets of supports coupled to a base upon which the valve is mounted.

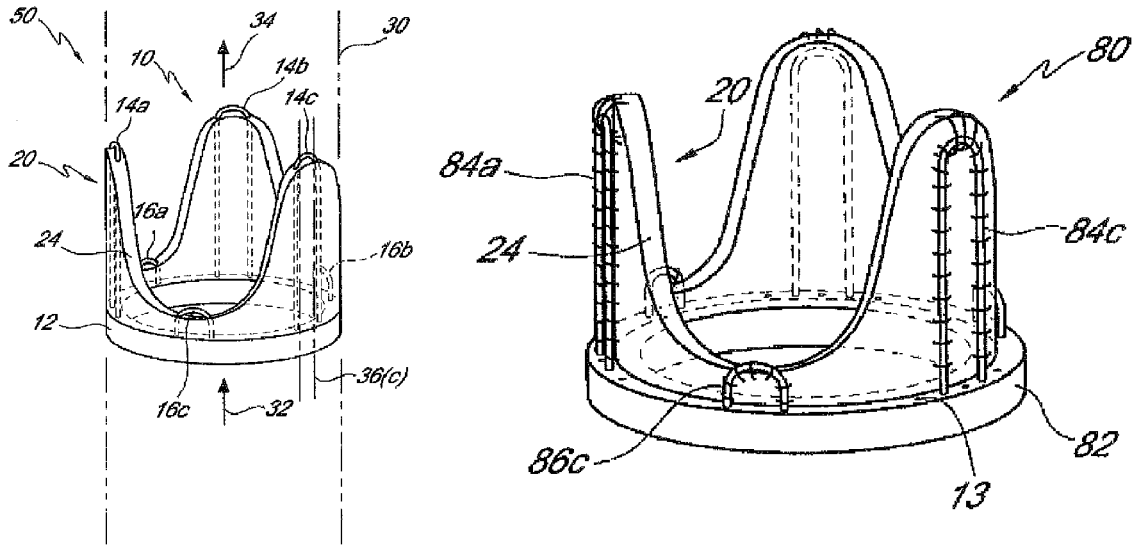

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 19, 35 and 36 is confirmed.

Claims 1, 6, 7, 10-13, 16-18, 20-23, 29-31 and 33 are cancelled.

Claims 2-5, 8, 9, 14, 15, 24-28, 32 and 34 were not reexamined.

* * * * *